(12) United States Patent
Chu

(10) Patent No.: US 10,740,441 B2
(45) Date of Patent: *Aug. 11, 2020

(54) MEDICINE CONTAINER WITH AN ORIENTATION SENSOR

(71) Applicant: SMRxT Inc., Orlando, FL (US)

(72) Inventor: Victor Chu, Orlando, FL (US)

(73) Assignee: SMRxT Inc., Orlando, FL (US)

( * ) Notice: Subject to any disclaimer, the term of this patent is extended or adjusted under 35 U.S.C. 154(b) by 302 days.

This patent is subject to a terminal disclaimer.

(21) Appl. No.: 15/673,792

(22) Filed: Aug. 10, 2017

(65) Prior Publication Data

US 2017/0337347 A1 Nov. 23, 2017

Related U.S. Application Data

(63) Continuation of application No. 13/827,373, filed on Mar. 14, 2013, now Pat. No. 9,740,828.

(Continued)

(51) Int. Cl.

| | |
|---|---|
| *G06F 19/00* | (2018.01) |
| *A61J 1/03* | (2006.01) |
| *G01G 15/00* | (2006.01) |
| *G01G 17/06* | (2006.01) |
| *G16H 20/13* | (2018.01) |
| *A61J 7/02* | (2006.01) |

(Continued)

(52) U.S. Cl.
CPC ............ *G06F 19/3456* (2013.01); *A61J 1/03* (2013.01); *A61J 7/02* (2013.01); *G01F 22/00* (2013.01); *G01G 15/00* (2013.01); *G01G 17/06* (2013.01); *G01G 19/00* (2013.01); *G01L 5/00* (2013.01); *G06F 19/3462* (2013.01); *G16H 20/13* (2018.01); *A61J 2200/30* (2013.01)

(58) Field of Classification Search
None
See application file for complete search history.

(56) References Cited

U.S. PATENT DOCUMENTS 9,182,582 B2 * 11/2015 Inoue ................. G02B 21/26
9,740,828 B2 * 8/2017 Chu ........................ A61J 1/03

(Continued)

FOREIGN PATENT DOCUMENTS

WO WO2006/086435 * 8/2006

OTHER PUBLICATIONS

Kong Y. Chen, The Technology of Accelerometry-Based Activity Monitors: Current and Future, 11 pages (Year: 2005).*

(Continued)

*Primary Examiner* — Tung S Lau
(74) *Attorney, Agent, or Firm* — Coats & Bennett, PLLC

(57) ABSTRACT

A medicine container configured to hold one or more different medications. The container may include an orientation sensor to determine the orientation of the container. The container may also include one or more additional sensors to detect other physical characteristics about the container and/or medicine. The orientation of the container in combination with the information from the one or more additional sensors is used to determine an accurate indication of an amount of the medicine within the container and thus usage information. The container also includes a wireless transmitter for transmitting the information regarding the medicine to a remote location.

7 Claims, 10 Drawing Sheets

Related U.S. Application Data

(60) Provisional application No. 61/780,483, filed on Mar. 13, 2013.

(51) Int. Cl.
    *G01F 22/00*     (2006.01)
    *G01G 19/00*     (2006.01)
    *G01L 5/00*     (2006.01)

(56) References Cited

U.S. PATENT DOCUMENTS

| | | | | |
|---|---|---|---|---|
| 10,254,265 B1 * | 4/2019 | Rezayat | ............... | G01N 33/146 |
| 2016/0262979 A1 * | 9/2016 | Wengreen | .......... | B65D 81/3841 |

OTHER PUBLICATIONS

Murtadha Aldeer, A Review of Medication Adherence Monitoring Technologies, 27 pages (Year: 2018).*
Chen Chen, a Medication Adherence Monitoring System for Pill Bottles Based on a Wearable Inertial Sensor, 4 pages (Year: 2019).*
Sensors for medical applications, 14 pages (Year: 2019).*
Dr. Chao Chen, Wireless Wearable Motion Sensor for Use in Medical Care 7 pages (Year: 2009).*

* cited by examiner

MEDICINE CONTAINER WITH AN ORIENTATION SENSOR

RELATED APPLICATIONS

This application is a continuation of application Ser. No. 13/827,373 filed Mar. 14, 2013, which claims the benefit of U.S. Provisional Application No. 61/780,483, filed on Mar. 13, 2013, each of which is hereby incorporated by reference in their entireties.

BACKGROUND

The present application is directed to a medicine container for holding medicine, and more particularly, to a medicine container with an orientation sensor that provides for accurate sensing an amount of medicine.

Various prior art medicine containers have been equipped to measure an amount of medicine that has been taken by a user and thus how much medicine is in the container. However, these containers have been plagued with issues.

These other medicine containers with sensors are used in an attempt to detect medicine usage. However, for accurate usage detection, the containers must be placed in a particular orientation, such as in an upright position with a bottom of the container positioned on a shelf or counter. If the containers are not in this particular orientation, the data sensed by the sensors is inaccurate. The sensors are not configured to determine whether the container is in the proper orientation. The sensors merely assume that the container is in the proper orientation at the time of measuring the data.

Other sensors have been used to detect specific actions involving the container. One embodiment includes a sensor that detects when a cap has been removed from a body of the container. The systems are configured to assume that this removal equates to the user taking their expected dosage of the medicine. However, this assumption is often wrong and results in poor medicine usage determinations. A user may open the container for a number of other reasons, including when the user opens the cap to check how much medicine is remaining and when the user inadvertently removes the cap.

These various sensor configurations are ineffective in accurately monitoring the medicine remaining the container and thus the medicine usage by the user. When this information is used to determine compliance by a particular user, the data is often completely off-base. Further, if an entire monitoring system such as that used by an insurance company or pharmaceutical manufacturer is based on information determined in these manners, the system is completely unreliable.

SUMMARY

The present application is directed to determining medicine usage based on an amount of medicine in a container. The medicine containers are equipped with one or more sensors that detect physical characteristics about the medicine in the container and the environment.

One embodiment disclosed in the present application is directed to a medicine container configured to hold medicine. The medicine container includes a body with exterior walls forming an interior space to hold the medicine. The container also includes an orientation sensor arranged within the body and configured to sense an orientation of the body in at least one axis. The container includes a quantity sensor arranged within the body and configured to sense a quantity of the medicine within the interior space with the quantity sensor configured to sense one of a weight of the medicine in the interior space or a volume of the medicine in the interior space. The container also includes a wireless communications interface arranged within the body and configured to send to a remote device readings from the orientation sensor, or the quantity sensor, or both, or information derived from the readings.

In one embodiment, the medicine container may also include a processor arranged within the body and configured to obtain readings from each of the orientation sensor and the quantity sensor at a plurality of time intervals.

In one embodiment, the processor may be further configured to determine medicine usage information based on the readings from each of the orientation sensor and the quantity sensor with the information communicated from the wireless communications interface being the medicine usage information.

In one embodiment, the processor may be configured to determine an orientation of the body based on one of the readings received from the orientation sensor and to cause the quantity sensor to sense one of the weight and the volume of the medicine in the interior space when the orientation of the body is in a predetermined orientation.

In one embodiment, the container may also include memory arranged within the body to store readings from each of the orientation sensor and the quantity sensor.

In one embodiment, the orientation sensor may be an accelerometer and may be positioned in the interior space.

In one embodiment, the container may include a module body arranged within the interior space and having a side that faces towards the exterior walls of the body with the module body being sized to fit within an outlet in the body, and with each of the orientation sensor, the quantity sensor, and the wireless communications interface being mounted on the module body.

In one embodiment, the container may include an environmental sensor arranged within the body and configured to sense an aspect of an environment in the interior space.

Another embodiment is directed to a monitoring system to determine medicine usage by a patient. The monitoring system includes a processor configured to obtain a first reading from an orientation sensor arranged within a container for containing medicine with the first reading being indicative of an orientation of the container, obtain a second reading from a quantity sensor arranged within the container with the second reading being indicative of a weight of the medicine in the container or a volume of the medicine in the container, and calculate a quantity of the medicine in the container based on the first reading and the second reading.

In one embodiment, the processor may be configured to determine that the container is in a predetermined orientation prior to calculating the quantity of the medicine in the container.

In one embodiment, the processor may be configured to determine a correction factor based on the orientation of the container and to calculate the quantity of the medicine in the container using the correction factor.

In one embodiment, the processor may be arranged within the container.

In one embodiment, the processor may be configured to cause a wireless communications interface arranged within the container to send and receive information about the medicine usage to a remote device.

In one embodiment, the processor may be configured to place the orientation sensor and the quantity sensor in a low-power state.

In one embodiment, the processor may be configured to obtain a third reading from an environmental sensor arranged within the container used to calculate the quantity of the medicine in the container based on the first, second, and third readings.

In one embodiment, the processor may be configured to receive the first and second readings from a wireless communications interface arranged within the container.

In one embodiment, the processor may be configured to notify the patient when the container is oriented outside of the predetermined orientation.

Another embodiment is directed to a medicine container configured to hold medicine. The container includes a body including exterior walls forming an interior space to hold the medicine. The container includes a first sensor arranged within the body and configured to sense an orientation of the body in at least one axis. The container also includes a second sensor arranged within the body and configured to sense a physical characteristic of the medicine indicative of an amount of the medicine in the body with the second sensor configured to sense the physical characteristic when the body is in a predetermined orientation sensed by the first sensor. The container includes a wireless communications interface arranged within the bottle to communicate information about the medicine with a remote device.

In one embodiment, the container may include a processor arranged within the body that receives signals from the first sensor indicating that the body is in the predetermined orientation and causes the second sensor to sense the physical characteristic of the medicine.

In one embodiment, the container may include a sensor module independent of the body and sized to fit within the interior space and be positioned in proximity to a bottom of the interior space and including an outer edge that faces towards the exterior walls of the body with the sensor module being mounted to the first and second sensors and the wireless communications interface.

In one embodiment, the second sensor may be a weight sensor or a volume sensor positioned in proximity to a bottom of the interior space and configured to sense a weight or a volume of the medicine within the interior space.

The various aspects of the various embodiments may be used alone or in any combination, as is desired.

DETAILED DESCRIPTION

The present application is directed to a medicine container configured to hold one or more different medications. The container may include an orientation sensor to determine the orientation of the container. The container may also include one or more additional sensors to detect other physical characteristics about the container and/or medicine. The orientation of the container in combination with the information from the one or more additional sensors is used to determine an accurate indication of an amount of the medicine within the container. The container also includes a wireless transmitter for transmitting information about the medicine to a remote location.

Figure 1:
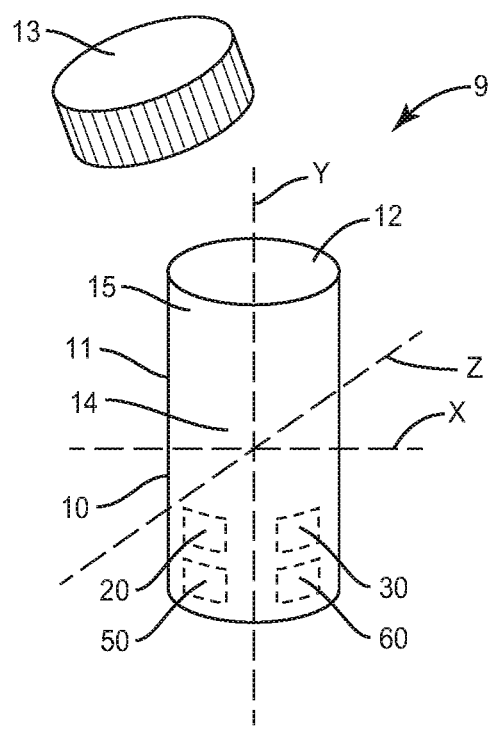
FIG. 1 is a perspective view of a medicine container.

FIG. 1 illustrates a container 9 with an interior space 14 to hold medicine. An orientation sensor 20 is configured to detect the orientation of a body 10 of the container 9 in one or more different axes X, Y, Z. Further, one or more additional sensors 30 are configured to detect one or more additional aspects about the container, the environmental conditions, and the medicine within the interior space 14. FIG. 1 includes the sensors 20, 30 positioned within the interior space 14. One or more of the sensors 20, 30 may also be positioned in a cap 13 that is attachable to a body 10 of the container 9, or connected to an exterior of the body 10. The information from the sensors 20, 30 is used to determine an amount of medicine within the container 9. The container 9 further includes a wireless transmitter 60 that transmits information about the medicine to a remote location. This information may be the actual medicine which is calculated by one or more components of the container 9. Alternatively, the information may be the sensor readings that are processed at a remote location where the medicine calculations are performed.

The container 9 may have a variety of different configurations for holding one or more different medications. The container 9 may be configured to hold medications of different physical forms, including but not limited to pills, tablets, capsules, gelatin, liquid, and powder. The container 9 may also be applicable for use with herbal medicines and supplements. The container 9 may include various configurations, including but not limited to containers 9 that are controlled by the user, such as a vial (as illustrated in FIG. 1), a bottle, and various packaging. The container 9 may also have a larger capacity and is controlled by an upstream entity, such as a care provider, pharmacist, doctor, insurer, or drug manufacturer. In one embodiment, the container 9 is a receptacle used at a pharmacy with a capacity to hold a relatively large amount of the medicine.

Figure 2:
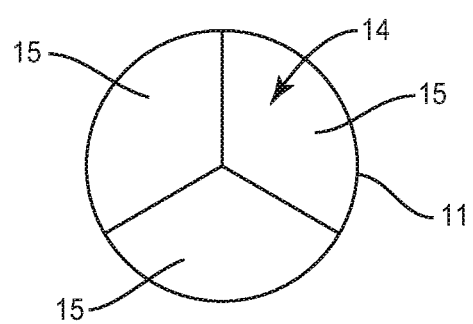
FIG. 2 is a schematic top view of an interior space of a medicine container divided into separate compartments.
Figure 3:
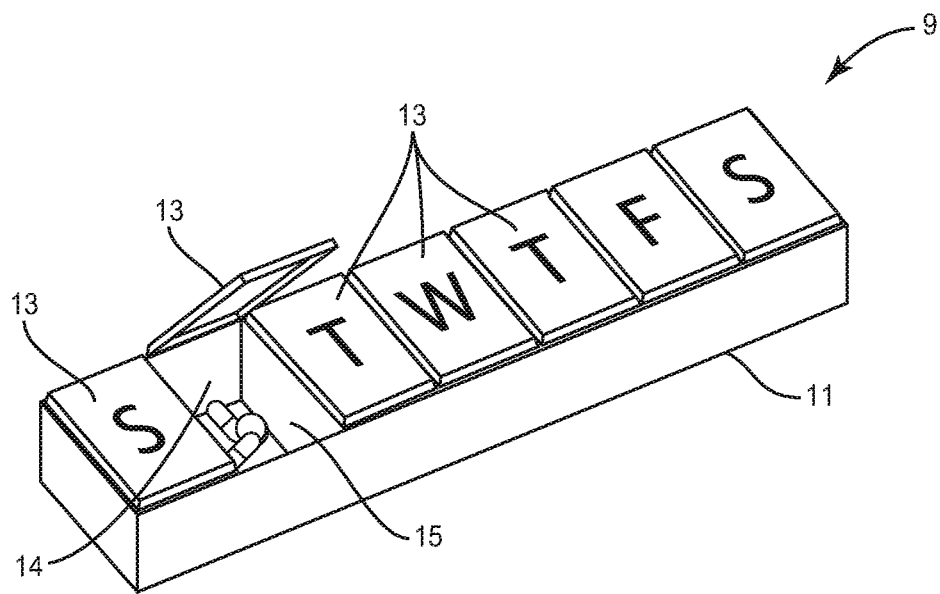
FIG. 3 is a perspective view of a medicine container.

The container 9 includes a body 10 with exterior walls 11 that form the interior space 14 to hold the medication. The body 10 also includes one or more outlets 12 for dispensing the medicine to a user. One or more caps 13 may be configured to attach to the body 10 and extend across the outlet 12 to prevent inadvertent removal of the medicine. The container 9 may be configured to hold a single type of medication, such as the vial as illustrated in FIG. 1 with the interior space 14 having a single compartment 15. The container 9 may also be configured with the interior space 14 divided into two or more separate compartments 15 to hold different types of medication, or separate doses of the same medicine. FIG. 2 illustrates a top view of a container 9 divided into different compartments 15 to segregate the medication. Other embodiments may include the container 9 divided into four sections, five sections, etc. FIG. 3 illustrates another embodiment that includes multiple different compartments 15 each having a separate cap 13. The container 9 includes compartments 15 that divide the medication into different groupings, such as different types of medication or different dosages of the same medication. FIG. 3 specifically includes a weekly medication container with each separate compartment 15 corresponding to a different day of the week. A user fills each of the compartments at the beginning of the week and is able to ensure the medicine is taken for each day of the week. The compartments 15 in the various embodiments may include the same or different shapes and/or sizes.

An orientation sensor 20 is integrated with the container 9 to determine the orientation measured as the inclination of the body 10 relative to two or more orthogonal axes against a known reference point, such as Earth, or Earth's gravity. In one embodiment, the orientation sensor 20 determines orientation relative to X, Y, and Z axes. In one embodiment, the orientation sensor 20 is an accelerometer that measures the proper acceleration of the device. The orientation of the body 10 may also be determined by various other types of orientation sensors 20. Examples include but are not limited to gyroscopes, magnetometers, analog and digital levels, and other various meters, levels, and switches.

The container 9 may include a single orientation sensor 20 that measures the orientation along one or more axes. In one embodiment, the orientation sensor 20 comprises a low-g accelerometer (e.g. +/−2 g) that measures the orientation along three separate axes. The device 10 may also include two or more accelerometers that each measures the orientation along different axes. The orientation sensor 20 may be positioned at various locations integrated with the container 9. In one embodiment, the orientation sensor 20 is positioned within the interior space 14. This positioning may protect the sensor 20 from external forces. The sensor 20 may also be positioned on the exterior of the body 10 or embedded within the exterior wall. In embodiments with multiple sensors 20, the sensors 20 may be positioned at the same or different locations. In one embodiment, the sensors 20 are spread around the interior space 14.

The one or more orientation sensors 20 are initially oriented correctly relative to the body 10. This provides for the one or more axes of the sensor 20 to coincide with the body 10. Using the example of FIG. 1, each sensor 20 may be orientated with each of its three axes aligned with axes X, Y, and Z. Alternatively, the sensors 20 may be placed in any orientation relative to the body 10. Prior to use, the sensors 20 are calibrated. One method includes placing the body 10 in a fixed position with respect to the ground and by using the measurements of the sensor 20 while in this position. The readings of the sensor 20 would then be adjusted to align with the three axes of the body 10.

In one embodiment, the container 9 includes just one or more orientation sensors 20.

The container 9 may further be equipped with one or more additional sensors 30. These additional sensors detect physical characteristics regarding the medicine in the interior space 14, the container 9, or environmental conditions. The one or more sensors 30 may be positioned at various locations about the container 9. In one embodiment, each of the sensors 30 is positioned within the interior space 14. This protects the sensors 30 from being dislodged or misplaced. This also places the sensors 30 in direct contact with the medication within the interior space 14. Alternatively, the sensors 30 may be positioned on the exterior of the body 10 or embedded within the body 10. Additionally, the sensors 30 may be positioned within the cap 13. In embodiments with multiple sensors 30, the sensors 30 may be positioned at the same or different locations. In one embodiment, the sensors 20 are spread around the interior space 14.

The container 9 may include multiple different sensors 20, 30 to detect the same physical characteristic. By way of example, the container 9 may include two or more orientation sensors 20, or two or more weight sensors 30. The data from the multiple sensors detecting the same aspect may be compared to determine that the data is consistent and reliable. Disparities in the sensors readings for the same physical aspect may indicate that at least one of the sensors is malfunctioning.

One type of sensor 30 detects the weight of the medicine in the interior space 14. The weight sensor 30 may use load, force applied to a surface. The weight sensor 30 may be configured to measure changes in electrical signals based on changes in force, torsion, or load placed on a strain gauge. The weight sensor 30 may be positioned within the interior space 14 and is acted upon by the medication. In one embodiment, the weight sensor 30 is positioned at a bottom of the interior space 14 away from the cap 13. This positioning provides for accurate weight detection when the body 10 is placed in an upright position, such as when it is set on a shelf or counter.

Another sensor 30 detects the volume of the medicine within the interior space 14. The volume sensor 30 may include various configurations for determining the level of the medicine within the interior space 14. Volume sensors 30 may be particularly applicable for detecting liquid medicine, although may also have good application for medicine in pill form and powder form. The volume sensor 30 may be configured to detect displacement and/or flow of the medicine to and from the interior space 14. The volume sensor 30 may also include ultrasonic or optical sensing components to detect a level of the medicine within the interior space 14. Components for sensing the volume of the medicine include but are not limited to level meters, switches, gauges, tactile sensors, float gauges, and pressure sensors and gauges.

Another sensor 30 detects the motion of the medicine in the interior space 14 and/or the motion of the container 9. Examples of motion sensors 30 include but are not limited to: passive and active infrared sensors; optical sensors including video and camera systems; radio frequency energy sensors using radar, microwave, and tomographic motion detection; sound detection using microphone and acoustic sensors; vibration sensors with triboelectric, seismic and inertia-switch sensors; and magnetism sensors using magnetic sensor or magnetometers.

Sensors 30 may also detect one or more different environmental conditions. Examples include but are not limited to temperature sensors 30 and humidity sensors 30.

The sensors 20, 30 may take multiple measurements to obtain accuracy in determining the various physical characteristics of the medicine. In one embodiment, the weight sensor 30 takes readings at about 15-100 times sampling rate per second with a resolution potential of about 0.001 grams. In another embodiment, a volume sensor 30 takes readings at about 15-100 times sampling rate per second with a resolution potential of 0.001 millimeters. In one embodiment, averages of the sensor readings are used in the determination process. In another embodiment, readings that are outside of an expected range are discarded as being bad. These readings may be discarded with the other acceptable readings being used for the calculations. The number of discarded readings may be monitored and notification sent to a remote party in the event the number reaches a predetermined number. This may indicate that the associated sensor 20, 30 is failing.

In containers 9 with a single compartment (e.g., FIG. 1), the container 9 may include a single sensor 20, 30 to detect the specific aspects. By way of example, the container 9 may include a single orientation sensor 20 and a single weight sensor 30. In containers 9 with multiple compartments 15, the container 9 may include separate sensors 20, 30 in the different compartments 15 to detect an aspect that is individualized to the specific compartment 15. In one embodiment, the container 9 includes a separate weight sensor 30 in each compartment 15. For aspects that are common amongst the different compartments 15, the container 9 may include a single sensor 20, 30. By way of example, the container 9 may include a single orientation sensor 20 or a single temperature sensor 30.

The container 9 may include multiple different sensors 30 to detect the same characteristic at different locations and/or times. In one embodiment, the container 9 includes multiple temperature sensors 30. One sensor 30 detects a temperature of the environment for purposes of determining a correction offset as will be explained below. A second sensor 30 detects a temperature in the interior space 14 to monitor temperature of the medicine. A third sensor 30 may detect a temperature at the location of the electrical components to monitor for overheating and possible failure.

The environmental sensors 30 may be used for a variety of different purposes. For example, a temperature sensor 30 may determine one or more temperatures to determine: a temperature of the medication, a temperature of the exterior environment; and a temperature of the electrical components.

Figure 4:
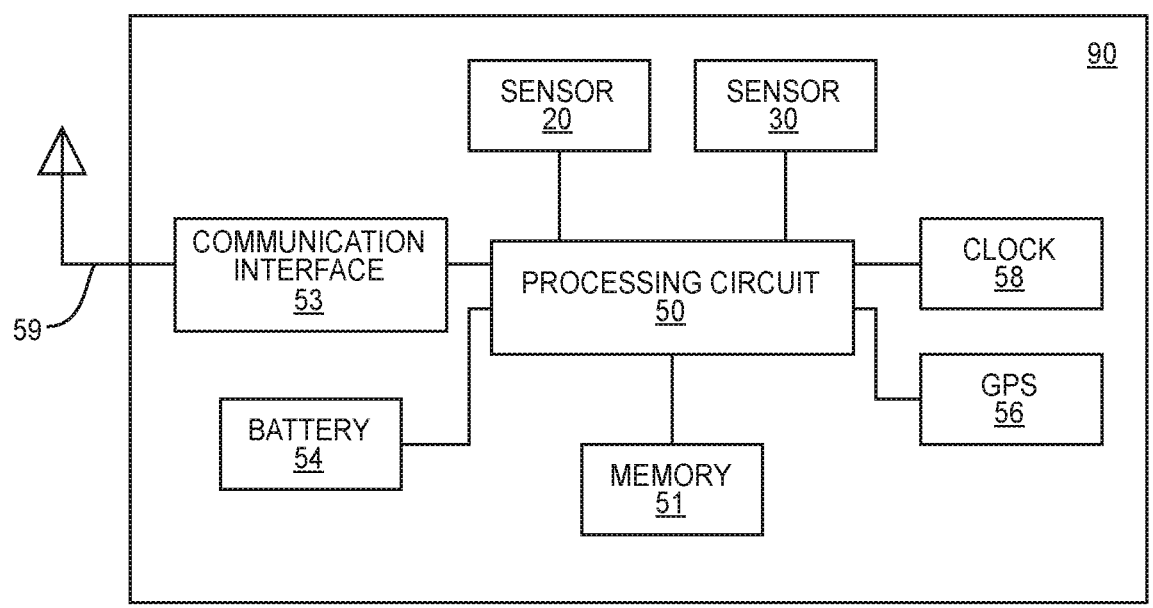
FIG. 4 is a schematic view of components of a medicine container.

FIG. 4 illustrates the components of a sensing circuit 90 according to one exemplary embodiment. The circuit 90 includes a processing circuit 50 that controls the overall operation of the container 9 according to program instructions stored in the memory 51 and may comprises one or more digital processing devices, such as microprocessors, microcontrollers, hardware, firmware, or a combination thereof. In one embodiment, the processing circuit 50 is configured to perform the calculations to determine the amount of medicine based on the one or more signals received from the one or more sensors 20, 30. In other embodiments, the processing circuit 50 is configured to cause the raw sensor readings to be transmitted to a remote location where the calculations are performed to determine the medicine usage. Memory may comprise both volatile and non-volatile memory for storing instructions and data needed for operation. Memory 51 may also store orientation information necessary to determine if the body 10 is in the proper orientation for accurately determining the medicine.

The communications interface 53 may comprise a short-range wireless interface, such as a BLUETOOTH interface, RFID, ZIGBEE, or WIFI interface, a long range cellular phone or satellite communications interface, or a wired interface, such as a serial, USB or FIREWIRE interface. There may be more than one communications interfaces 53.

The sensing circuit 90 may include a GPS receiver 56 or other location detector to determine location and history of locations. A clock 58 is associated with the processing circuit 50 that measures the various timing requirements for specific events. The clock 58 may be independent from the processing circuit 50 as illustrated in FIG. 4. In another embodiment, the clock 58 is incorporated within the processing circuit 50. A battery 54 is provided to power the various container components 54.

Figure 4A:
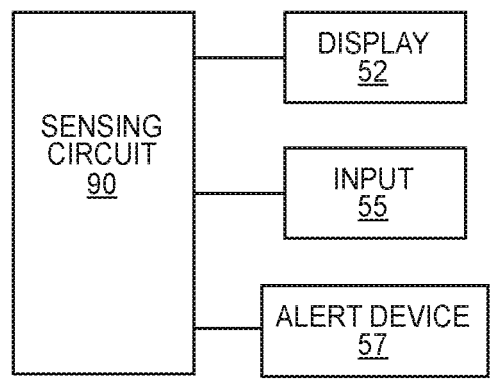
FIG. 4A is a schematic view of components communicatively coupled with a sensing circuit.

As illustrated in FIG. 4A, the container 9 may also include additional components that are associated with the sensing circuit 90. A display 52 may be configured to display information to the user and/or medical provider. The display 52 may comprise a liquid crystal display (LCD) or an organic light emitting diode (OLED). Additionally, the display 52 may use printed electronic displays, electronic paper displays, or electronic ink technology to provide a thin, flexible and durable display to enable users to view information.

Some embodiments of the container 9 may additionally include one or more user input devices 55 indicated generally by the numeral 55. User input devices 55 may comprise any known input device including buttons, keypads, touch pads, wheels, dials, mouse devices, trackballs, etc. A touch screen display could also be used for user input. Imaging systems and motion or movement systems for recognizing hand gestures, and voice recognition systems may also be used for receiving user input.

The container 9 may also include or control one or more alerting devices 57 for alerting the user of specified events or conditions. The alerting devices 57 may comprise indicator lights that illuminate or generate lighting effects, speakers, beepers, buzzers, or other sound devices; and vibrators or other tactile devices. The alerting devices 57 are controlled by the processing circuit 50 to notify the user when predetermined events or conditions occur. The alerts can be personalized and customized by the user to distinguish the alerts. In one embodiment, alerting device 57 includes an indicator light that is illuminated when the user has not taken their medication within a predetermined time period.

Figure 4B:
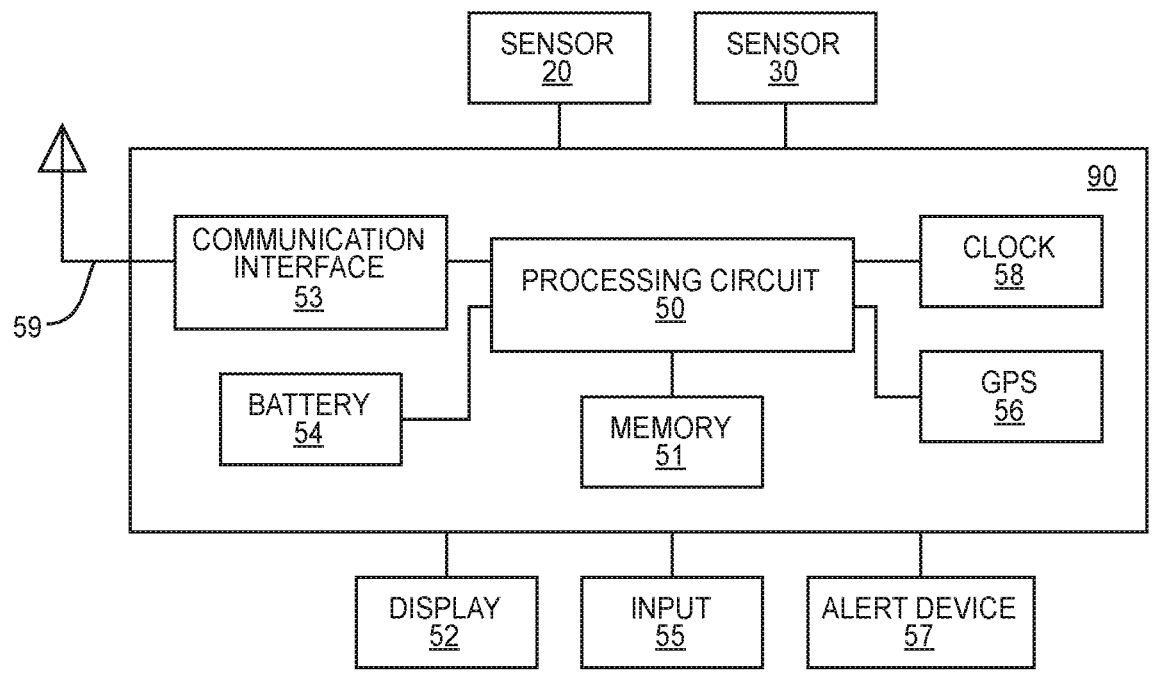
FIG. 4B is a schematic view of components communicatively coupled with a sensing circuit.

FIG. 4B schematically illustrates another embodiment of the various components of the container 9. The sensing circuit 90 includes the processing circuit 50, memory 51, communication interface 53, battery 54, GPS 56, and clock 58. The sensors 20, 30 are separate components that are communicatively coupled to the sensing circuit 90. The display 52, input device 55, and alert device 57 are also separate components communicatively coupled to the sensing circuit 90.

The configuration of the sensing circuit 90 and the various components that are included in the sensing circuit 90 and are communicatively coupled to the sensing circuit 90 may vary.

A drawback of previous devices that do not determine orientation is the variability in the weight or volume detected as a result of the orientation of the body 10. The detected weight of the medication will be less if the body 10 is angled on its side such that a portion of the medicine positioned away from the weight sensor 30. The same amount of medication will register a greater weight if the body 10 is in an orientation with the medicine being positioned over the weight sensor 30. Likewise, the volume of the medicine may be improperly determined based on the orientation of the body 10.

Figure 5A:
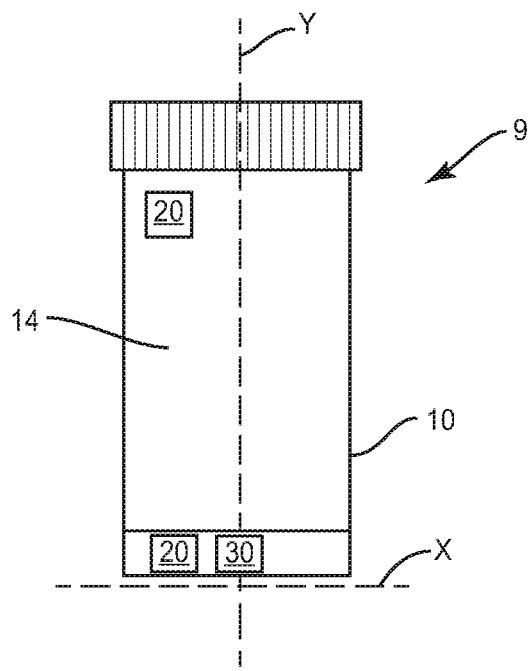
FIG. 5A is a schematic view of a medicine container in a first orientation.
Figure 5B:
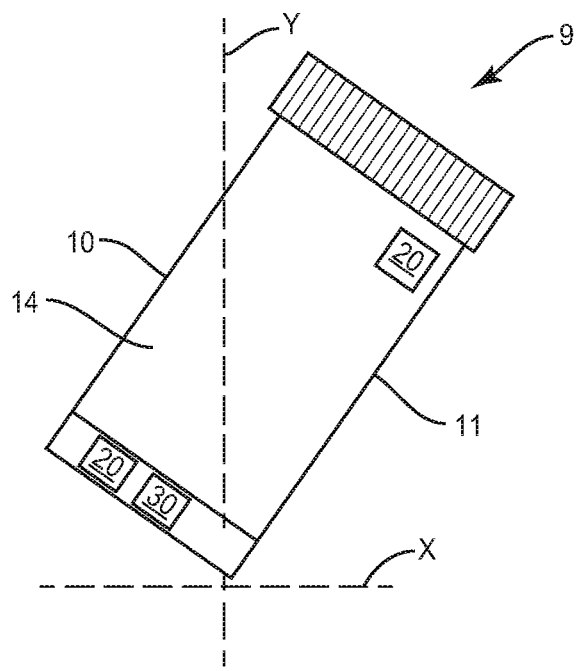
FIG. 5B is a schematic view of a medicine container in a second orientation.

FIGS. 5A and 5B illustrate a container 9 positioned in different orientations. In these embodiments, the container 9 includes a weight sensor 30 positioned within at a bottom of the interior space 14. FIG. 5A illustrates the body 10 positioned in an upright orientation. This orientation provides for the weight sensor 30 to accurately detect the amount of medicine within the interior space 14 because of the positioning of the medicine over the weight sensor 30. This orientation may result from the container 9 being placed upright on a level surface such as a countertop in a drawer, or while being held by the user.

FIG. 5B illustrates the body 10 in a tilted orientation which would result in an inaccurate weight determination by the weight sensor 30 if read by the weight sensor 30 alone. The inaccuracy results because the medicine within the interior space 14 is not positioned over the weight sensor 30. At least a portion of the medicine is being supported by the exterior wall 11 away from the weight sensor 30. This orientation may occur when the container 9 is stored in a purse or luggage, or when held in this orientation by the user.

The same concepts apply to a determination of the medicine using a volume sensor 30. The volume sensor 30 may be configured to obtain accurate readings when the body 10 is in a particular orientation, such as an upright orientation as illustrated in FIG. 5A. Readings taken by the volume sensor 30 when the body 10 is tilted away from the upright position may result in inaccurate results.

Figure 6A:
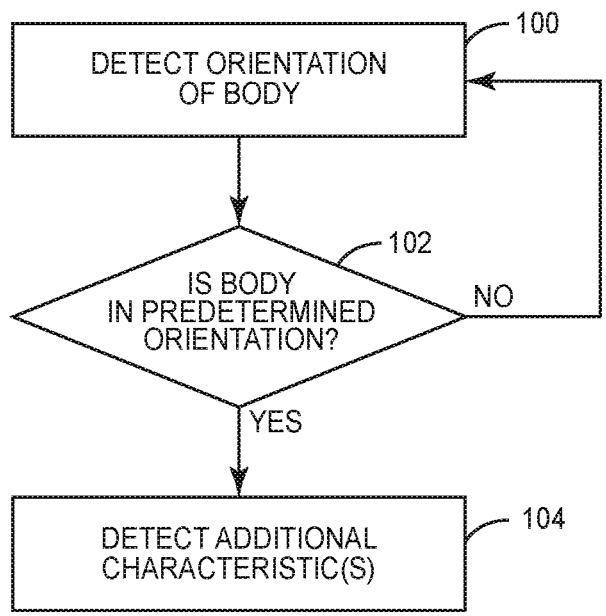
FIG. 6A is a flowchart diagram of a process of detecting information about medicine stored in a container.

FIG. 6A illustrates one process of detecting an amount of medicine within the interior space 14. The orientation of the body 10 is determined by the orientation sensor 20 (step 100). This may include readings from a single orientation sensor 20, or multiple orientation sensors 20. Further, the orientation may be over a range of time, such as over the last 5 seconds, or may be the orientation at a particular point in time.

A determination is then made as to whether the body 10 is in a predetermined orientation (step 102). The predetermined orientation may be a specific orientation within one or more axes. By way of example, the predetermined orientation may be in the upright position with no deviation away from a vertical axis that extends through the container 9 (e.g., axis Y in FIG. 1). Alternatively, the predetermined orientation may include a range of orientations that provide for reliable data. An example may include+/−5 relative to a vertical axis. This determination is based on the readings from the one or more orientations sensors 20. The orientation calculations using the raw sensor data may be performed by the one or more sensors 20, or by the processing circuit 50 that receives the signals from the one or more sensors 20. The calculation may also be performed at a remote location with the data being sent through the communication interface 53.

If the body 10 is not in the predetermined orientation, an alert may be sent electronically to a messaging system to notify the user of this condition. The alert may include activating the alert device 57 and/or indicating a message on the display 52. Further, another orientation detection will occur. The subsequent detection may occur immediately after a determination that the initial orientation is not acceptable. The subsequent detection may also occur after a time delay that is established by the one or more sensors 20 or the processing circuit 50.

If the body 10 is in the proper orientation, the additional characteristic regarding the medicine will be detected (step 104). This determination may be performed by one or more sensors 30, such as one or more weight sensors 30 or one or more volume sensors 30. The calculations to convert the raw sensor data to the one or more physical characteristics may be performed at one or more of the sensors 20, 30, the processing circuit 50, and a remote location as explained above for the orientation readings.

In one embodiment, all of the readings from the sensors 20, 30 may not be sent to the remote device when the body 10 is not within the predetermined orientation. For example, just the orientation information may be sent to the remote device.

Figure 6B:
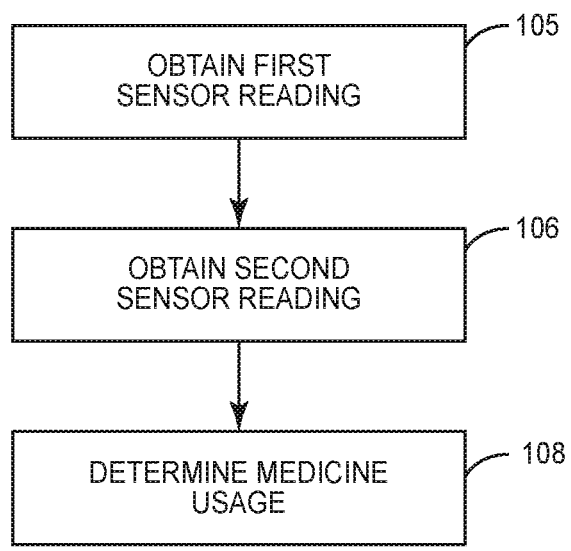
FIG. 6B is a flowchart diagram of a process of detecting information about medicine stored in a container.

FIG. 6B illustrates another embodiment of determining an amount of medicine in the interior space 14. Readings are obtained from the first sensor 20 (step 105) and the second sensor(s) 30 (step 106). These readings from the sensors 20, 30 are obtained regardless of the orientation of the body 10. The information is then used to determine the amount of medicine (step 108). This determination may be performed regardless of the orientation of the body 10. In another embodiment, the orientation is performed just when the body 10 is in a predetermined orientation. If the body 10 has not been in the predetermined orientation for a predetermined period of time or for a predetermined number of readings, an alert may be sent to the user and/or remote party indicating this occurrence.

The orientation and physical characteristic detection may be performed at various times. In one embodiment, this data is detected at periodic time periods that may be on a regular schedule (e.g., every 30 minutes) or at random times (e.g., 5 times daily at random times). In one embodiment, a schedule for the user to take the medication is stored in memory 51. The processing circuit 50 then checks for usage at various times corresponding to the scheduled time periods. In another embodiment, these characteristics are determined once a day, such as at the end of day (e.g., midnight).

The data may also be determined based on a request from an outside source. This may include the processing circuit 50 receiving a signal through the communication interface 53 from an outside source. This may be from a doctor, caregiver, pharmacist, insurance company, or other like party, computing system, or program who is authorized to check the compliance of the user in taking the medication. This may also be from a friend or relative checking on whether the user is taking their medicine. In one specific embodiment, the user is an elderly person living alone and the compliance may be monitored by one of his/her children.

The information may also be obtained after a motion sensor 30 or activity and orientation detected by the changes in the orientation sensor 20 integrated with the container 9 detects that a movement beyond a predetermined amount. This detection of this motion implies that the user has taken a dosage of the medicine. One example of the movement may include when the container 9 is angled beyond a predetermined amount relative to a given axes. Another embodiment obtains the orientation and weight data after a sensor 30 detects that the cap 13 has been removed from and/or placed back onto the body 10.

In one embodiment, when the data is to be measured and the body 10 is not in the predetermined orientation, a subsequent orientation determination will occur. These subsequent measurements may occur at various times as described above. Additionally, the user may be notified when a proper orientation reading does not occur. This notification may occur through the alert device 53 and include various mechanisms, such as but not limited to lighting an indicator on the exterior of the container 9, and emitting an audible sound. A message may also be displayed on the display 52 to further indicate to the user that the orientation detection has been unsuccessful. This may include an icon or message being displayed to the user.

In one embodiment of the body 10, the processing circuit 50 causes a message to be sent to a remote party. The message results in the remote party directly or indirectly getting in contact with the user and informing them to place their medicine container 9 in an orientation that allows for the weight to be detected. This may also provide for the remote party to determine the status of user. For example, the user may have experienced a medical emergency which is the reason why the container 9 has not been placed in the proper orientation. The remote party is able to determine this during their contact and provide for medical attention as necessary.

The processing circuit 50 may further include information about specific aspects of the medication within the interior space 14. The initial weight of the medication placed into the interior space 14 may be stored in memory 51. The processor 50 is then able to determine an amount of medicine removed from the container 9 based on the differences in weight between the current weight and the previous weight. In one embodiment when the medicine is in pill form, the weight of each pill may also be stored in memory 51. The processing circuit 50 is then able to determine the number of pills taken by the user based on the differences in weight between the current amount and a previous amount.

Figure 7:
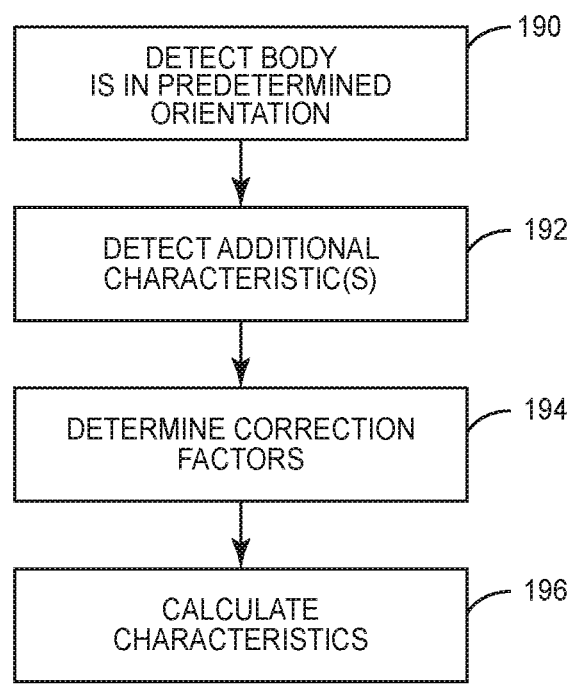
FIG. 7 is a flowchart diagram of a process of detecting information about medicine stored in a container.

The final determination of the one or more physical characteristics may require factoring in one or more correction offsets based on additional sensed data. FIG. 7 illustrates one embodiment of a process that factors in correction offsets. The process includes detecting that the body 10 is in the predetermined orientation (step 190) and detecting one or more additional characteristics about the medicine, container, or environment (step 192). These additional characteristics affect the calculations required to determine the physical characteristics. In one embodiment, this includes the temperature, humidity, or pressure. Data may be stored in memory 51 that equates the sensed characteristic to a correction factor to be applied when calculating the amount of medicine (step 194). In one embodiment, a pressure above a certain amount may affect the volume of the medicine. The raw sensor data is then computed with the one or more correction factors included in the calculation to determine the amount of medicine (step 196). These one or more correction offsets are based on characteristics detected by additional sensors 30.

In another embodiment, the offset may account for the body 10 being titled away from a predetermined position as detected by the orientation sensor 20. Correction factors may be applied for a wide variety of angular variations away from a specific orientation. By way of example, a first correction factor is applied to a weight of the medicine when the body 10 is angled+/−5° from upright. This is caused by a portion of the medicine being misaligned with the weight sensor 30. A greater correction factor is applied to calculate a weight when the body is angled+/−10° from upright. These allowed angular ranges fall within the predetermined orientation, but require a correction offset to be applied to calculate an accurate value.

This process of including the correction factors may occur regardless of the orientation of the body 10. Alternatively, use of the correction factors may occur just when it is determined that the body 10 is in a predetermined orientation.

Figure 8:
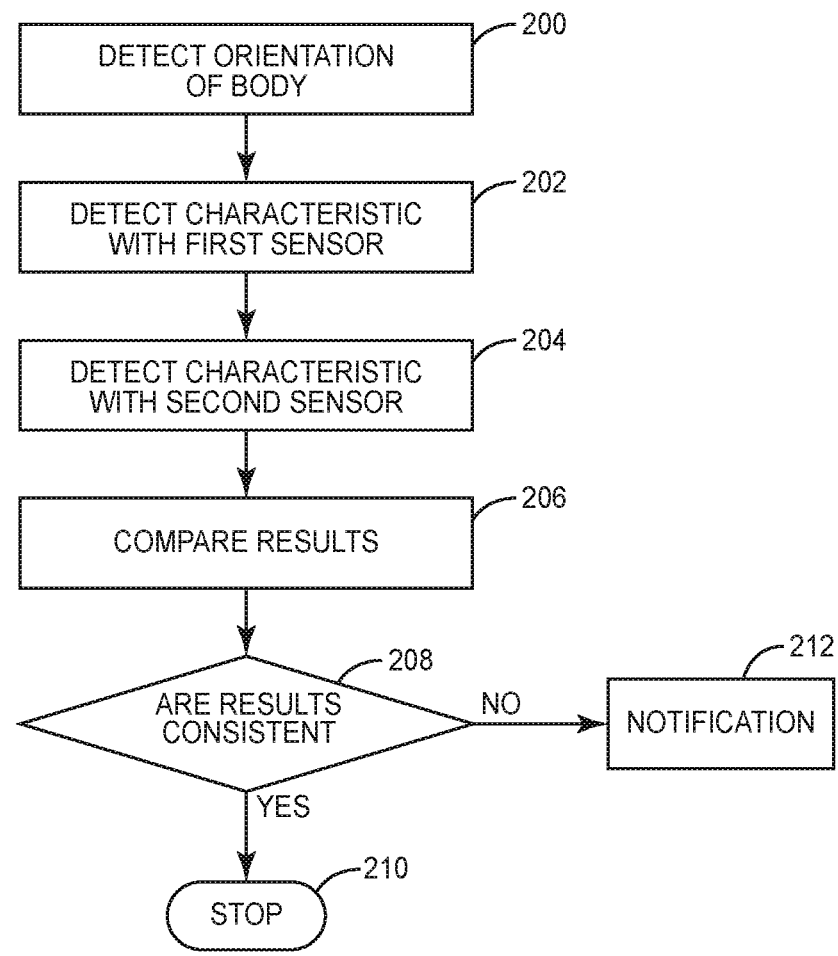
FIG. 8 is a flowchart diagram of a process of comparing results from two sensors.

The container 9 may include multiple sensors 30 that each detect a particular characteristic. The readings from these different sensors 30 may be compared to ensure that the sensors 30 are operating properly. FIG. 8 illustrates one such process. The process includes detecting that the body 10 is within a predetermined orientation (step 200). A characteristic is determined by a first sensor 30 (step 202) and the same characteristic is determined by a second sensor 30 (step 204). The first and second sensors 30 may be the same, or they may be different. For example, the first sensor 30 may detect volume based on a float switch, and the second sensor 30 may detect volume based on an optical sensor. The raw sensor data for each sensor 30 is calculated by one or more of the sensors 30, processing circuit 50, and remote device.

The results are then compared, either by the processing circuit 50 or a remote device (step 206) to determine if they are consistent (step 208). Consistent results occur when the detected medicine amounts are substantially the same or within a predetermined range (e.g., 5%, 10%, 15%). If the results are consistent, then the processing circuit 50 or remote device confirms the accuracy of the sensors 30 and the testing processes stops (step 210). If the results are not consistent, the processing circuit 50 or remote device determines that one or both sensors 30 are defective and a notification is sent (step 214). The notification may be sent to one or more of the user, pharmacist, monitoring server, physician, and guardian.

The processing circuit 50 may be configured to place one or more of the components of the container 9 in an inactive mode when not in use. In one embodiment, the inactivated components may include one or more sensors 20, 30. Other embodiments may include placing additional or other components in an inactive mode. The inactive mode may occur because there have been no activation events within a predetermined period of time.

In one embodiment, the processing circuit 50 periodically determines the orientation of the container 9 based on readings from the orientation sensor 20. The processing circuit 50 will place one or more of the components in the inactive mode if the orientation has not changed within a given time period (e.g., 10 minutes, 30 minutes, 1 hour, 5 hours, 10 hours, 24 hours, 48 hours, etc.). In another embodiment, the processing circuit 50 determines whether the container has moved based on readings from a motion sensor 30. The processing circuit 50 will place one or more of the components in the inactive mode if the container 9 has not moved within a given time period (e.g., 10 minutes, 30 minutes, 1 hour, 5 hours, 10 hours, 24 hours, 48 hours, etc.).

The inactive mode uses a lower amount of power than when the various components are functioning in an active mode. In one embodiment, the sensors 20, 30 in an active mode perform detection routines on a predetermined basis (e.g., every 10 minutes, every 30 minutes, every hour, every 5 hours, every 5 hours, every 10 hours, etc.). In one embodiment, all functionality of the sensors 20, 30 is off when the sensors 20, 30 are in an inactive mode and therefore draw no power from the battery 54. Another embodiment provides for the sensors 20, 30 to have partial functionality. In one embodiment, the orientation sensor 20 remains active while the one or more additional sensors 30 are placed in the inactive mode.

Placing the one or more sensors 20, 30 or components (such as communications interface 53, display 52, etc.) in the inactive mode provide a number of advantages. One main advantage is the inactive mode draws less power from the battery 54 thus prolonging its use.

In another embodiment, the processing circuit 50 is in an inactive mode. The sensors 20, 30 are each configured to periodically take readings at the same time or about the same time. These readings are paired together and stored in memory 51. The processing circuit 50 is further configured to periodically transmit the information via the communication interface 53 to a remote device. The information may be transmitted at various intervals (e.g., 10 minutes, 30 minutes, 1 hour, 5 hours, 10 hours, 24 hours, 48 hours, etc.).

Figure 9:
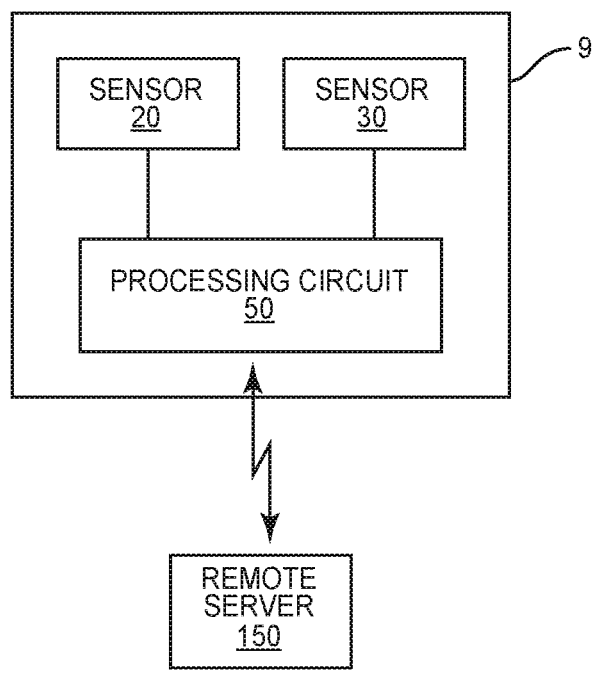
FIG. 9 is a schematic view of a container communicatively coupled to a remote device.

The processing of the raw sensor data from the various sensors 20, 30 may occur at a variety of elements within the system. As illustrated in FIG. 9, the sensors 20, 30 may include circuitry and processing capacity to processing the raw sensor data and determine the various aspects regarding the medication associated with the container 9. The processing circuit 50 is further configured to process the raw sensor data. Further, the raw sensor data may be forwarded from the container 9 (through the communication interface 53) to a remote device 150, such as a server, where a portion or all of the calculations are performed by associated circuitry.

Figure 10:
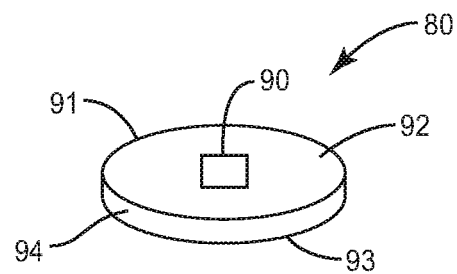
FIG. 10 is a schematic view of a sensing module.

The sensors 20, 30 may be part of a sensing module 80 as illustrated in FIG. 10. The sensing module 80 is a separately positioned within the interior space 14 and attached in position. The sensing module 80 includes a body 91 that includes a top side 92, an opposing bottom side 93, and a side wall 94. The body 91 may include a cross-sectional shape that substantially matches the cross-sectional shape of the interior space 14 to facilitate insertion into, alignment, and attachment to the body 10. The sensing circuit 90 may be included with the sensing module 80 and mounted or otherwise attached to the body 91.

Figure 11:
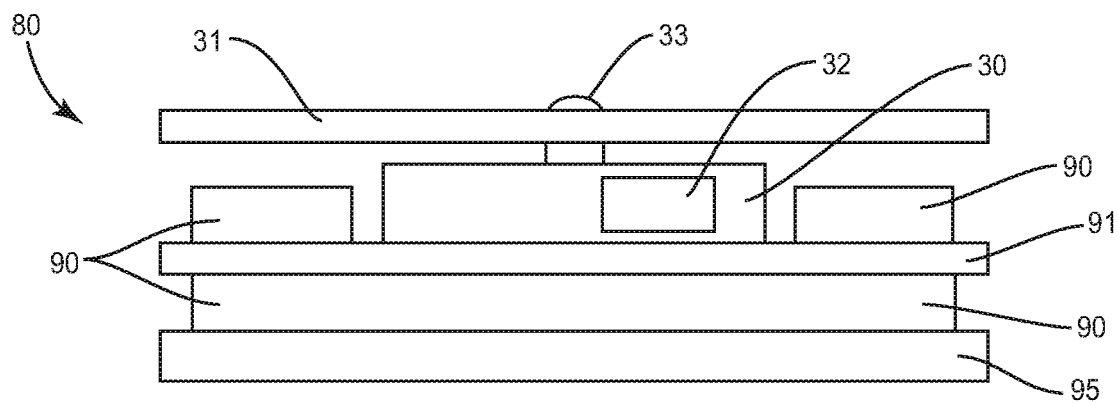
FIG. 11 is a side view of a sensing module.
Figure 11A:
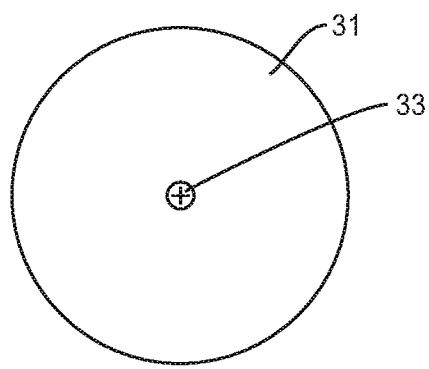
FIG. 11A is a top view of the sensing module of FIG. 11.
Figure 11B:
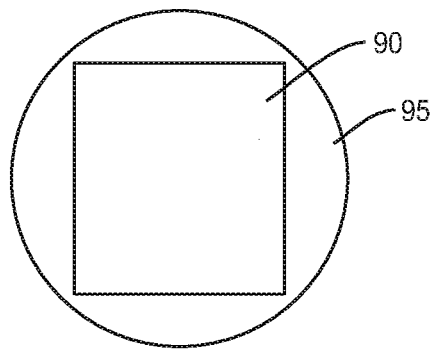
FIG. 11B is a bottom view of the sensing module of FIG. 11.

FIG. 11 illustrates a side view of one specific sensing module 80 sized to fit within the body 10. The sensing module 80 includes a weight sensor 30 positioned at a top side and including a scale plate 31 that is mounted with a fastener 33 to the weight sensor 30 and sensor circuitry 32. The body 91 is positioned on a bottom side of and supports the weight sensor 30. Additional elements of the sensing circuit 90 are positioned on the body 91. The sensing module 80 may further include a second body 95 that may be the same as or different than the body 91. FIG. 11A illustrates a top view of the sensing module 80 of FIG. 11 with the scale plate 31 being shaped to conform to the cross-sectional shape of the interior space 14. FIG. 11B likewise illustrates a bottom view of the sensing module 80 of FIG. 11.

Figure 12:
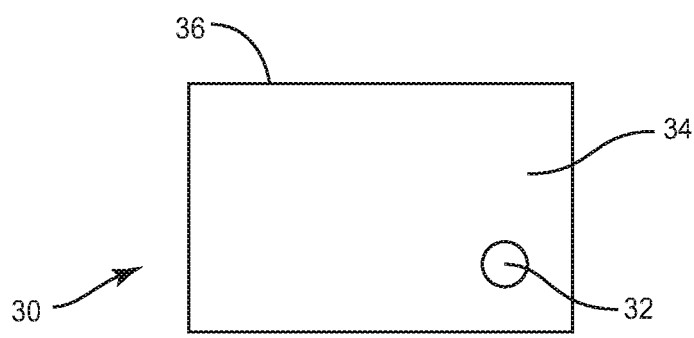
FIG. 12 is a schematic view of a weight sensor.

FIG. 12 generally discloses a weight sensor 30 that includes a body 34 sized to fit within the interior space 14 of the body 10. The body 34 includes an upper surface 36 configured to receive the force exerted by the medicine. A processing circuit 32 may be positioned within the body 34 and configured to obtain the raw sensor data. Processing circuit 32 may further be configured to perform one or more calculations with the data.

Figure 13:
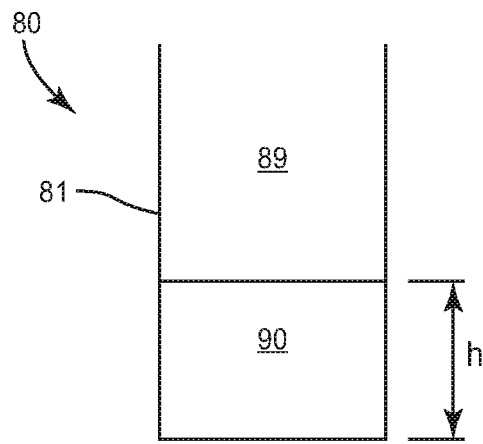
FIG. 13 is a schematic view of a sensing module.

FIG. 13 includes a schematic view of a sensing module 80 configured to fit within a body 10. The sensing module 80 includes a body 81 that includes an interior space 89 sized to hold medicine. The sensing circuit 90 is positioned below the interior space 89. In one embodiment, the sensing circuit 90 includes a height h of about 0.25 inches.

Figure 14:
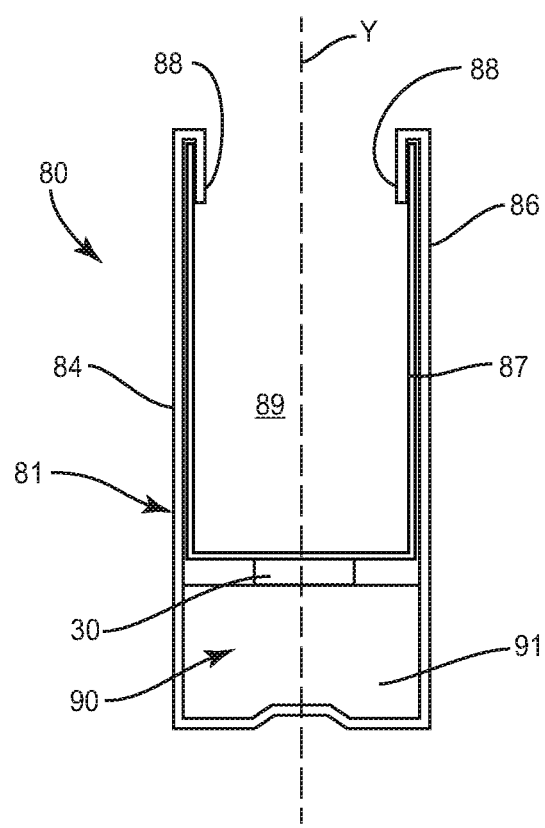
FIG. 14 is a side view of a sensing module.

FIG. 14 includes another embodiment of a sensing module 80 sized to fit within the interior space 14 of the body 10. The module 80 includes a body 81 with an outer section 86 and an inner section 87. The inner section 87 forms an interior space 89 sized to hold medicine. Further, the inner section 87 is configured to move along an axis Y relative to the outer section 86. A top edge of the section 86 includes a lip 88 to position the top edge of the inner section 87. The lip 88 protects the inner section 87 and provides for its movement relative to the outer section 86.

A weight sensor 30, such as a load cell, is positioned between the sections 86, 87 to determine a weight of the medicine within the interior space 89. In the embodiment of FIG. 14, the weight sensor 30 is positioned on a body 91 of the sensing circuit 90, or can be positioned inside the body 91.

Figure 15:
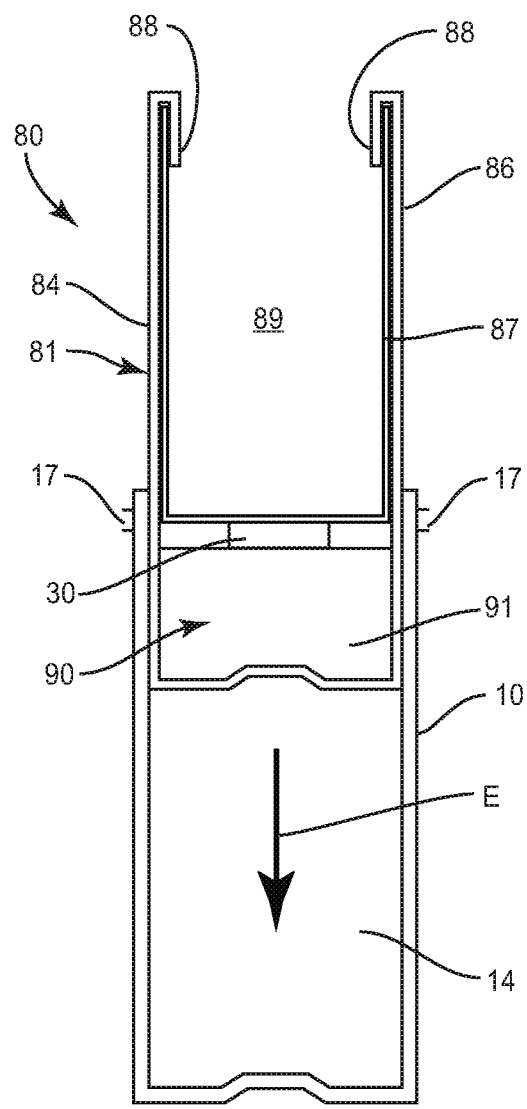
FIG. 15 is a side view of a sensing module being lowered into an interior space of a body.

FIG. 15 illustrates the sensing module 80 being positioned within the body 10. The sensing module 80 is sized to be inserted in the direction of arrow E into the interior space 14 through the outlet 12 of the body 10. As illustrated, the size of the sensing module 80 corresponds to the body 10 to provide a secure fit. Once fully mounted, the lip 88 may align with the top edge of the body 10. The cap 13 (not illustrated) is mounted to connections 17 such as threads on the body 10 and is sized to extend across the sensing module 80 to prevent inadvertent escape of the medicine.

The module 80 may be secured within the body 10 in a variety of different manners. Examples include but are not limited to mechanical fasteners, adhesives, snap-fit, and friction fit. In one embodiment, the exterior of the outer section 86 includes threads that mate with corresponding threads on the interior of the body 10. This provides for the sensing module 80 to be screwed into the body 10.

The sensing module 80 may be used on existing medicine bodies 10 that do not include sensor capabilities. The sensing module 80 is inserted into the body 10 and secured to provide for this functionality.

In one embodiment, the container 9 may further be configured to notify the user and/or a remote party if a predetermined environmental condition is detected. For example, if a temperature in the interior space 14 is detected to be at or above a predetermined amount, or the humidity in the interior space 14 is at or above a predetermined amount, the container 9 may send a notification. This may be particularly applicable to biologic, living medicines and/or medicines that are sensitive to extreme conditions that may expire when exposed to these conditions.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A medicine container configured to hold medicine, the medicine container comprising:
 a body including exterior walls forming an interior space to hold the medicine;

an accelerometer arranged within the body and configured to sense an acceleration of the body;

a quantity sensor arranged within the body and configured to sense a quantity of the medicine within the interior space;

a wireless communications interface arranged within the body and configured to communicate with a remote device; and a processing circuit configured to obtain a plurality of paired readings from the wireless communications interface that were taken by the accelerometer and the quantity sensor;

wherein the processing circuit is configured to determine an amount of medicine remaining in the interior space based on the readings from the quantity sensor taken just when the body is both level and upright and not when the body is not level and not upright based on the readings from the accelerometer.

2. The medicine container of claim 1, wherein the processing circuit is arranged within the body.

3. The medicine container of claim 1, wherein the processing circuit is configured to obtain the plurality of paired readings from the wireless communications interface.

4. The medicine container of claim 1, wherein the quantity sensor is configured to sense one of a weight of the medicine in the interior space or a volume of the medicine in the interior space.

5. The medicine container of claim 1, further comprising an environmental sensor arranged within the body and configured to sense an aspect of an environment in the interior space.

6. The medicine container of claim 5, wherein the processing circuit is further configured to apply a correction offset based on readings from the environmental sensor to determine the amount of medicine remaining in the interior space.

7. The medicine container of claim 1, further comprising memory arranged within the body to store the readings from each of the accelerometer and the quantity sensor.

* * * * *